US006417341B1

(12) United States Patent
Anders et al.

(10) Patent No.: US 6,417,341 B1
(45) Date of Patent: *Jul. 9, 2002

(54) MALARIA MEROZOITE ANTIGEN SUBUNIT VACCINE

(75) Inventors: Robin Fredric Anders, North Melbourne; Pauline Elizabeth Crewther, North Carlton; Mary Shu Mai Leet, Flemington; Anthony Neil Hodder, Ocean Grove; David Pye, Bullengarook, all of (AU)

(73) Assignee: Saramane Pty., Ltd., Victoria (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/687,387

(22) PCT Filed: Feb. 3, 1995

(86) PCT No.: PCT/AU95/00049

§ 371 (c)(1),
(2), (4) Date: Oct. 7, 1996

(87) PCT Pub. No.: WO95/21192

PCT Pub. Date: Aug. 10, 1995

(30) Foreign Application Priority Data

Feb. 4, 1994 (AU) ............................................. PM 3689

(51) Int. Cl.[7] ........................ C07H 21/04; C07K 14/00; A61K 39/00; C12N 15/00
(52) U.S. Cl. ................. 536/23.5; 424/184.1; 424/268.1; 424/272.1; 424/130.1; 424/278.1; 424/192.1; 435/252.3; 435/172.3; 435/69.1; 435/69.3; 435/342; 435/252.33; 435/235.1; 435/325; 536/23.1; 536/23.7; 530/350; 530/300; 935/18; 935/31; 935/41; 935/58
(58) Field of Search ........................... 424/184.1, 268.1, 424/272.1, 130.1, 278.1, 192.1; 435/252.3, 69.1, 69.3, 320.1, 342, 172.3, 252.33, 235.1, 325, 69.8, 71.2; 536/23.1, 23.7, 23.5; 530/350, 300; 935/18, 31, 41, 58, 65, 73, 81

(56) References Cited

U.S. PATENT DOCUMENTS 4,879,213 A * 11/1989 Fox et al.
4,999,422 A * 3/1991 Galliher

OTHER PUBLICATIONS

Anders et al, Vaccine, 16/2–3:240–247, 1998.*
Rogers et al. Vaccine 17:3136–3144, 1999.*
Shi et al, PNAS, 96:1615–1620, 1999.*
Hodder et al, JBC, 271/46:29446–29452, 1996.*
Lehninger in Biochemistry, 2nd Ed. Worth Publishers New York, NY (1975) on p. 63.*
Lazar et al.*
Burgess et al.*

Eisen & Immunology, 2nd Ed. Harper & Row Publishers, Hagerstown, PA (1980).*
Cox (1991)Tibtech 9, 389.*
Plotkin, S.A. et al, (Ed) Published by W. B. Saunders Company (Philadelphia)—1988, 571.*
Mitchell Parasitology (1989) 98, S29.*
Kaslow, Immunology Letters (1990) 25, 83.*
International Search Report.
Clin. Exp. Immunol. 49, pp. 297–309, (1982), Deans J.A. et al, "Rat Monoclonal Antibodies Which Inhibit the in Vitro Multiplication of *Plasmodium Knowlesi*".
Parasite Immunology, 10, pp. 535–552 (1988), Deans J. A. et al, "Vaccination Trials in Rhesus Monkeys With a Minor, Invariant, *Plasmodium Knowlesi* 66kD Merozoite Antigen".
Molecular and Biochemical Parasitology, 39 pp. 279–284 (1989) Marshall, V M et al, "Structure of the Apical Membrane Antigen 1 (AMA–1) of *Plasmodium Chabaudi*".
Molecular and Biochemical Parasitology, 39 pp. 279–284, (1990), Peterson, M G et al, "Apical Membrane Antigen of *Plasmodium Fragile*".
Molecular and Biochemical Parasitology, 65 pp. 183–187 (1994), Cheng, Q and Saul. A, "Sequence Analysis of the Apical Membrane Antigen 1 (AMA–1) *Plasmodium Vivax*".
Molecular and Cellular Biology vol. 9(7); pp. 3151–3154, (Jul. 1989), Peterson, M G et al., "Integral Membrane Protein Located in the Apical Complex of *Plasmodium Falciparum*".
Molcular and Biochemical Parasitology, 42, pp. 285–288 (1990), Thomas, A W et al, "Analysis of Variation in PF83, an Erthrocytic Merozite Vaccine Candidate Antigen *Plasmodium Falciparum*".
Molecular and Biochemical Parasitology, 13, pp. 187–199 (1984), Thomas, A W et al, "The Fab Fragments of Monoclonal IgG to a Merozite Surface Antigen Inhibit *Plasmodium Knowles* Invasion of Erythrocytes".
Journal of Biological Chemistry, vol. 265(29); pp. 17974–17979, (Oct. 15, 1990), Waters, A P et al, "A Merozoite Receptor Protein from *Plasmodium Knowlesi* if Highly Conserved and Distributed Throughout *Plasmodium*".
AU 30699/89 B (627448) (Saramane PTY LTD, Aug. 27, 1992.
AU 74471/91 A (The United States of America) Sep. 18, 1991.

* cited by examiner

Primary Examiner—Nita Minnifield
(74) Attorney, Agent, or Firm—Sughrue Mion, PLLC

(57) ABSTRACT

An immunogenic polypeptide for use in inducing an immune response against Plasmodium infection comprises an amino acid sequence corresponding to a non-full length fragment of the apical membrane antigen 1 (AMA-1) of Plasmodium species which does not include a transmembrane domain thereof, and which is stabilised by folding thereof. Production of the immunogenic polypeptide by expression of a recombinant DNA molecule in a host cell, and methods and compositions using the immunogenic polypeptide are disclosed.

10 Claims, 7 Drawing Sheets

SEQUENCE LISTING

```
<160> NUMBER OF SEQ ID NOS:   5

<210> SEQ ID NO 1
<211> LENGTH: 18
<212> TYPE: DNA
<213> ORGANISM: Plasmodium chabaudi
```

```
<400> SEQUENCE: 1
cagataaaat tatttcag                                                    18

<210> SEQ ID NO 2
<211> LENGTH: 15
<212> TYPE: DNA
<213> ORGANISM: Plasmodium chabaudi

<400> SEQUENCE: 2
agtccaataa atcag                                                       15

<210> SEQ ID NO 3
<211> LENGTH: 25
<212> TYPE: DNA
<213> ORGANISM: Plasmodium falciparum

<400> SEQUENCE: 3
agaattattg ggaacatcca tatca                                            25

<210> SEQ ID NO 4
<211> LENGTH: 24
<212> TYPE: DNA
<213> ORGANISM: Plasmodium falciparum

<400> SEQUENCE: 4
cataaaccaa cttatgataa aatg                                             24

<210> SEQ ID NO 5
<211> LENGTH: 1412
<212> TYPE: DNA
<213> ORGANISM: Plasmodium vivax

<400> SEQUENCE: 5
gccttgtgca cattgggaag tgcgggcgaa accagaagcc gagcaggctg acccgtagcg       60
ccaacaacgt tctactggaa aagggcccta ccgttgagag aagcacacga atgagtaacc      120
cctggaaagc gttcatggaa aaatacgaca tcgaaagaac acacagttct ggggttcgag      180
tggatttagg ggaagatgca gaagtggaaa atgcaaagta cagaattcca gctggaagat      240
gtcctgtttt tggaaagggt atcgtcatag agaattccgc tgttagcttc ttaacccctg      300
tggctacagg agatcagagg ctgaaggatg gaggtttcgc cttccccaaa gcggatgacc      360
atatctcccc catgacatta gcgaacctta aggaaaggta taaagacaat gtagagatga      420
tgaagttaaa cgatatagct ttgtgcagaa cccacgcagc tagctttgtc atggcagggg      480
atcaaaattc gtcctacaga cacccagctg tatacgacga aaagaataaa acatgccaca      540
tgttgtattt atcagcgcag gaaaatatgg gtccgaggta ctgcagctca gatgcacaaa      600
atagagatgc cgtgttctgc ttcaagccag ataaaaatga aagctttgaa acctggtgt       660 atttgagcaa aaatgtgcgt aatgattggg ataaaaaatg cccccgtaaa aatttaggaa      720
acgccaagtt cggattatgg gtggatggga actgcgaaga aattccatac gttaaagaag      780
tggaggcaaa ggatctgcgc gaatgcaatc gaatcgtttt cggagcgagt gcctcagatc      840
aaccaactca gtatgaagaa gaaatgacgg attatcaaaa aatacaacaa gggttttagac     900 aaaacaaccg agagatgatt aaaagtgcct ttcttccagt gggtgcattc aactcggata      960
atttcaaaag taaggaagga ggatttaact gggcaaattt cgattctgta aaaaataagt     1020
gttacatttt taataccaaa ccgacttgcc tcattaatga caaaaatttt attgcaacaa     1080
cggcgttatc tcacccacaa gaagtagacc cggagttccc ctgcagcata tataaagacg     1140
```

-continued

```
aaattgaaag agaaattaag aaacaatcga ggaacatgaa tctgtacagt gttgatgggg   1200
aacgcattgt cctgccgagg atatttatct ccaacgataa ggagagtatc aaatgtccct   1260
gcgaacctga gcacatttcc aacagtacct gcaactttta cgtttgtaac tgtgtagaga   1320
aaagggcgga aattaaggaa aataaccaag ttgttataaa ggaagaattt agggattatt   1380
acgaaaatgg ggaggaaaaa tcgaacaagc ag                                 1412
```

MALARIA MEROZOITE ANTIGEN SUBUNIT VACCINE

FIELD OF THE INVENTION

This invention relates to a non-naturally occurring immunogenic polypeptide derived from a merozoite antigen of Plasmodium species, and to methods of production thereof. The invention also relates to the use of this immunogenic polypeptide in a subunit vaccine against malaria.

BACKGROUND OF THE INVENTION

Apical membrane antigen 1 (AMA-1) of Plasmodium species (previously also referred to as RMA-1) is a merozoite protein that is considered a leading candidate for inclusion in a malaria vaccine (see International Patent Publication No. WO 89/07645). AMA-1 is found associated with the merozoite apical organelles but subsequently it relocates to the merozoite surface prior to merozoite invasion of the erythrocyte. Early studies with PK66, the homologue of AMA-1 expressed in the simian parasite *Plasmodium knowlesi*, showed that merozoite invasion could be inhibited with a monoclonal antibody to AMA-1[1,2] and that immunization with the purified parasite antigen provided partial protection of rhesus monkeys against infection with *P. knowles*[3].

The AMA-1 gene sequence has been determined for a number of different isolates of *P. falciparum*[4,5] and for several other Plasmodium species[6-8]. The deduced amino acid sequence is typical of a type I integral membrane protein with an $NH_2$-terminal signal sequence and a presumed transmembrane domain towards the COOH-terminus. A comparison of the various AMA-1 sequences shows this to be a relatively conserved protein which contrasts with MSA-1 and MSA-2, two other well characterised merozoite surface antigens. In the large $NH_2$-terminal, presumably ectodomain, there are 16 cysteine residues that are conserved in all AMA-1 sequences. This indication that folding of the ectodomain is stabilised by intramolecular disulphide bonds is supported by the observation that the mobility of AMA-1 on SDS-PAGE varies depending on whether or not the sample buffer contains a reducing agent.

Because AMA-1 is relatively conserved in the genus it has been possible to identify clones corresponding to the homologue in other species of Plasmodium. Thus, AMA-1 of the simian malaria, *P. fragile*[7] and the murine malaria *P. chabaudi adami*[6] are available for studies of vaccine efficacy using appropriate host-parasite combinations. Because of the presumed disulphide bonded structure, the AMA-1s of both *P. fragile* and *P. chabaudi* were expressed in insect cells using recombinant baculovirus to produce antigen for use in preclinical vaccine trials. The *P. fragile* AMA-1 expressed in this way was isolated by lentil lectin chromatography and then anion- and cation-exchange chromatography. Saimiri monkeys immunized with the semi-purified molecule were partially protected against challenge with *P. fragile*. In this trial the degree of protection among immunized monkeys was positively correlated with the titre of antibodies induced by immunization. All surviving monkeys were drug-treated to eliminate persisting parasitaemias and re-challenged with *P. falciparum*. Three of four control monkeys developed transient, low parasitaemias whereas no *P. falciparum* parasitaemias were detected in the five immunized animals that were re-challenged. Thus, immunization with *P. fragile* AMA-1 provides protection against the homologous parasite and also may provide some cross-immunity against *P. falciparum* over and above that provided by a prior infection with *P. fragile*.

Subsequently, the protective efficacy of AMA-1 was studied in mice using the *P. chabaudi* homologue of AMA-1. Initially, the full-length *P. chabaudi* AMA-1 was expressed in insect cells using recombinant baculovirus and a vaccine trial was carried out using a lysate of insect cells infected with the recombinant baculovirus (In preliminary experiments cell lysates induced antibody responses that approached those induced by the semi-purified *P. fragile* antigen). C3H/He mice immunized with insect cell lysates containing the *P. chabaudi* AMA-1 were protected against challenge with *P. chabaudi*. None of the immunized mice died and peak parasitaemias were very much lower than those in mice that were immunized with lysates of insect cells infected with non-recombinant baculovirus.

Although it may be possible to base a vaccine against *P. falciparum* infections of humans on baculovirus-expressed full-length *P. falciparum* AMA-1, there are several disadvantages to using this approach for a human vaccine. First, it is more expensive to use a eukaryotic expression system than it is to use *E. coli* as the host cell. Second, the antigen is glycosylated in insect cells and this introduces microheterogeneity into the protein which could make it difficult to manufacture reproducible batches of purified material. Third, AMA-1 is a type I integral membrane protein and therefore the full-length molecule would be difficult to work with in aqueous buffers without added detergent. In view of the above disadvantages, the present inventors have examined the possibility of producing AMA-1 in *E. coli* in a form soluble in aqueous buffers and capable of inducing a protective immune response.

SUMMARY OF THE INVENTION

According to the present invention there is provided a non-naturally occurring immunogenic polypeptide comprising an amino acid sequence corresponding to a non-full length fragment of the apical membrane antigen 1 (AMA-1) of Plasmodium species, said polypeptide not including an amino acid sequence corresponding to the transmembrane domain of AMA-1 and being stabilised by folding.

Folding of the polypeptide is preferably achieved by generation of intramolecular disulphide bonds which stabilise the polypeptide in a conformation required for inducing a protective immune response.

The amino acid sequence of the immunogenic polypeptide corresponding to a non-full length fragment of AMA-1, may be a fragment corresponding to the mature ectodomain of the antigen not including the transmembrane domain thereof, or a portion thereof.

Preferably, the AMA-1 fragment is a fragment of *P. falciparum* AMA-1, however the present invention also extends to AMA-1 fragments of other Plasmodium species, including *P. vivax*, *P. fragile* and *P. chabaudi adami*

Preferably also, the AMA-1 fragment is a fragment which contains at least two of the conserved cysteine residues of the AMA-1 molecule. It will be appreciated, however, that the fragment may contain from two to all of the sixteen conserved cysteine residues of AMA-1.

The immunogenic polypeptide in accordance with this invention is preferably produced by recombinant DNA technology.

Accordingly, in another aspect the present invention provides a recombinant DNA molecule comprising a nucleotide sequence which encodes a polypeptide comprising an amino acid sequence corresponding to a non-full length fragment of the apical membrane antigen 1 (AMA-1) of Plasmodium species, said polypeptide not including an amino acid sequence corresponding to the transmembrane domain of AMA-1.

The recombinant DNA molecule may also comprise an expression control sequence operatively linked to the nucleotide sequence as described above.

The present invention also extends to a recombinant DNA cloning vector containing a recombinant DNA molecule as broadly described above, as well as to a host cell such as *E. coli* containing such a recombinant DNA molecule or recombinant DNA cloning vector. Such a host cell, of course, provides means for the production of the immunogenic polypeptide of the present invention using techniques which are well known to persons skilled in this art.

As an alternative to the prokaryotic host cell, the recombinant DNA molecule of this invention may be cloned using a eukaryotic host cell such as yeast, with folding and disulphide bond formation being achieved by passage of the expressed polypeptide through the secretory pathway of the cells.

It has been found that a stabilised conformation is required to enable the AMA-1 fragment to induce a protective response, and accordingly where the immunogenic fragment is produced as a recombinant product, particularly in a prokaryotic expression system, refolding of the product with disulphide bond formation is required to produce an efficacious immunogenic polypeptide.

In work leading to the present invention, the present inventors have discovered a fragment of AMA-1 corresponding to the mature ectodomain which, when expressed in *E. coli*, purified by Ni-chelate chromatography, refolded by dilution in the presence of reduced and oxidized glutathione, concentrated by anion-exchange chromatography, and injected formulated with an appropriate adjuvant, induces an immune response which protects against malaria.

Accordingly, the present invention extends to a vaccine composition, or composition for inducing an immune response in a host, comprising an immunogenic polypeptide as broadly described above, and a pharmaceutically acceptable carrier or diluent. Such a vaccine composition preferably also comprises an adjuvant.

The formulation of such vaccine compositions is well known to persons skilled in this field. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and it is described, by way of example, in *Remington's Pharmaceutical Sciences*, 18th Edition, Mack Publishing Company, Pennsylvania, USA. Except insofar as any conventional media or agent is incompatible with the active ingredient, use thereof in the vaccine compositions of the present invention is contemplated. Supplementary active ingredients can also be incorporated into the compositions.

The present invention also provides a method for actively immunizing a host against Plasmodium infection, which comprises administering to the host an effective amount of a vaccine composition as described above.

The active component is administered in prophylactically effective amounts. A prophylactically effective amount means that amount necessary at least partly to attain the desired effect, that is to induce an immune response against Plasmodium infection. Such amounts will depend, of course, on individual patient parameters including age, physical condition, size, weight and concurrent treatment. These factors are well known to those of ordinary skill in the art and can be addressed with no more than routine experimentation.

Throughout this specification, unless the context requires otherwise, the word "comprise", or variations such as "comprises" or "comprising", will be understood to imply the inclusion of a stated integer or group of integers but not the exclusion of any other integer or group of integers.

DETAILED DESCRIPTION OF THE INVENTION

Studies with *P. chabaudi* AMA-1 have provided evidence that a fragment of AMA-1 corresponding to the mature ectodomain, when expressed in *E. coli*, purified by Ni-chelate chromatography, and refolded by dilution in the presence of reduced and oxidized glutathione is an antigen of particular interest as a potential subunit vaccine against human malaria. The results indicate that the $NH_2$-terminal domain (presumed ectodomain) of AMA-1 alone is sufficient to induce a protective immune response. Thus, there is no requirement to express the full-length polypeptide which, being a type I integral membrane protein, has solubility characteristics that make it difficult to purify using aqueous buffers and conventional chromatographic procedures. The results also indicate that the ectodomain of AMA-1 has a conformation stabilised by intramolecular disulphide bonds and that this conformation (or a related conformation stabilised by disulphide bonds) is required to induce a protective immune response. Because of the reducing environment in the cytosol of bacteria, recombinant proteins expressed in *E. coli* or other prokaryotic host cells usually do not fold with the correct disulphide-bonding pattern. Because of this, it is usual to utilise eukaryotic expression systems to generate appropriately folded proteins with multiple intramolecular disulphide bonds. Although the disulphide bonding pattern in AMA-1 has not been established, it is clear that the refolding procedure used in these studies results in the formation of intramolecular disulphide bonds that are critical for generating epitopes recognized by antibodies induced by malaria infections of mice. As a reduced and alkylated protein was incapable of inducing a protective immune response, it is also clear that intramolecular disulphide bonds generated in the *E. coli*-expressed recombinant AMA-1 ectodomain are critical for creating epitopes that induce protective immune responses.

In the accompanying drawings:

FIG. 1 is a schematic diagram of the AMA-1 polypeptide showing the relationship of the insect cell (Bv) and *E. coli*-expressed forms of AMA-1 to the parasite protein.

FIG. 2 shows SDS-PAGE of purified and refolded AMA-1B run under reduced (1) and non-reduced (2) conditions. Panel A: Coomassie blue stained gel (2 $\mu$g of protein in each lane). Panel B; Immunoblot probed with hyperimmune mouse serum (0.2 $\mu$g protein in each lane).

Figure 6:
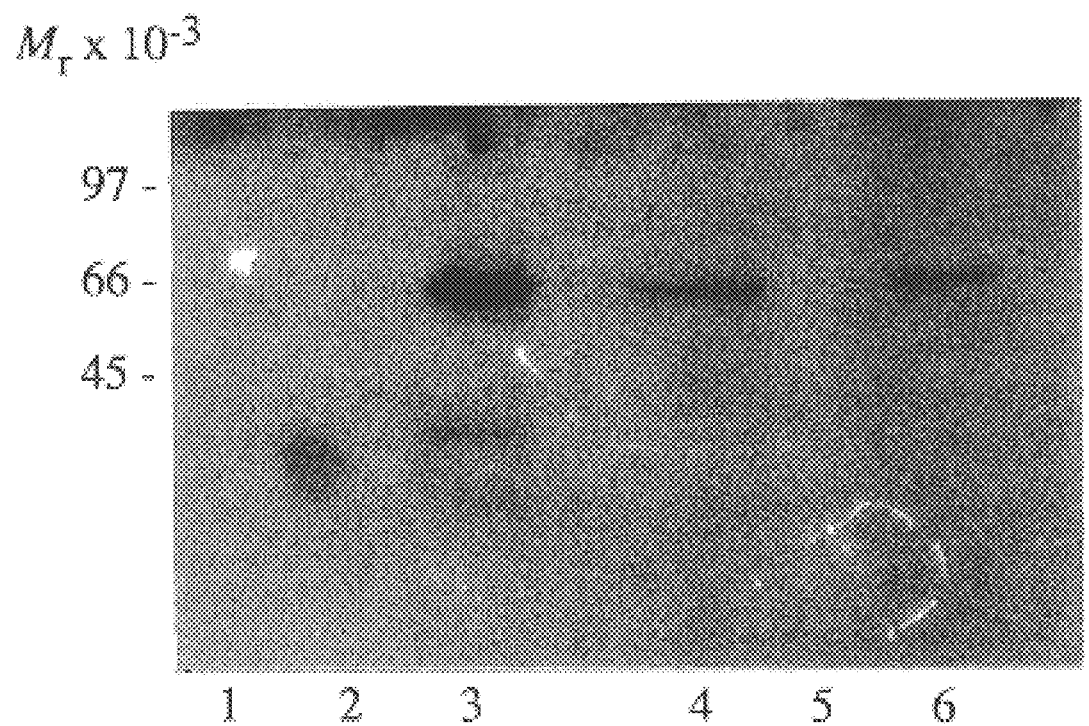

FIG. 6 shows immunoblot analyses of the effect of refolding on the antigenicity of *P. falciparum* AMA-1B. Non-folded (lanes 1 and 4), reduced and alkylated (lanes 2 and 5) and refolded (lanes 3 and 6) AMA-1B was subjected to SDS-PAGE on a 12.5% gel and then transferred to a nitrocellulose membrane which was probed with a pool of serum from adult Papua New Guinean blood donors, (approximately 0.06 µg protein in each lane).

Figure 7:
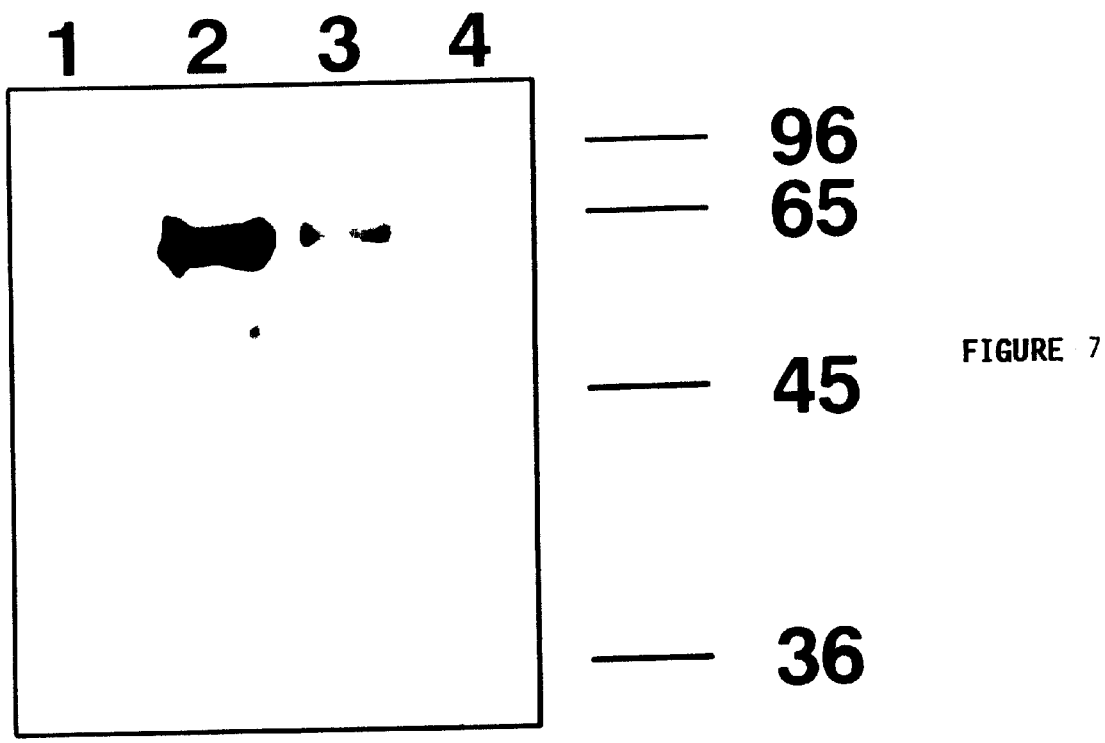

FIG. 7 shows Coomassie blue stained SDS-PAGE of purified fractions containing *P. vivax* AMA-1B (lanes 2, 3 and 4) and size markers.

Figure 8:
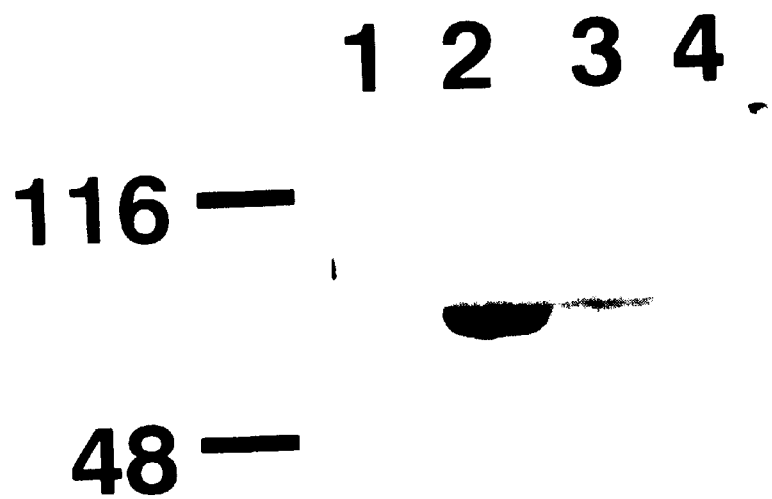

FIG. 8 shows Western blot of gel equivalent to FIG. 7 showing Coomassie blue stained material is *P. vivax* AMA-1B.

Further features of the present invention will be apparent from the detailed description in the following Examples.

EXAMPLE 1

*P. chabaudi* AMA-1

Materials and Methods

Expression

DNA encoding the $NH_2$-terminal domain of the AMA-1 expressed by the murine parasite *P. chabaudi adami* strain DS was amplified from genomic DNA by the PCR using Pfu DNA polymerase and oligonucleotides corresponding to nucleotides 622–640 (SEQ ID NO: 1) and 1971–1986 (SEQ ID NO: 2) of the published sequence[6]. The amplified DNA was cloned into the expression vector pDS56/RBSII, 6× his which was then used to transform *E. coli* strain JPA101. Six 600 ml fermentation batches were prepared. The cells were isolated by centrifugation and the batches of wet *E. coli* paste were stored frozen for subsequent isolation of the recombinant protein.

Purification of Recombinant AMA-1B

*E. coli* were lysed with lysozyme and sodium deoxycholate in the presence of PMSF as described by Sambrook et al.[9]. The insoluble inclusion bodies were isolated by centrifugation and washed with Triton X-100 and EDTA also as described by Sambrook et al.[9]. The washed inclusion bodies were solubilized by incubation for >1 hr in 6M guanidine-HCl, 10 mM Tris-HCl, pH 8.0. After centrifugation the supernatant was filtered (0.22 um) and loaded onto a 10 ml column of Ni-agarose. The Ni-agarose was washed successively with 6M guanidine-HCl, 10 mM tris-HCl pH 8.0, pH 6.3 and pH 5.9 before the protein was eluted in the same buffer adjusted to pH 4.5. The fractions eluted from the column were analysed by SDS-polyacrylamide gel electrophoresis and those containing the highest concentrations of protein were pooled and stored at −20° C.

Refolding Recombinant AMA-1 B

The pooled fractions from the Ni-chelate chromatography were thawed and diluted approximately 1:100 in ice-cold 100 mM Tris-HCl, pH 8.0 containing 1 µM reduced glutathione to give a final protein concentration of 50 µg/ml. After a 2 min incubation on ice, oxidized glutathione was added to give a final concentration of 0.25 µM and the solution was incubated under nitrogen at room temperature for 16 hr. After dialysis overnight against 10 mM Tris-HCl, pH 8.0 the refolded protein was incubated in a batch with 10 ml DEAE-Sepharose equilibrated with the same buffer. The anion exchanger was transferred to a column and washed with 10 mM Tris-HCl, pH 8.0 until the effluent gave a stable baseline at OD 280 nm. The refolded AMA-1B was then eluted with 10 mM Tris-HCl, pH 8.0 containing 0.5 M NaCl and stored aliquoted at −70° C.

Reduction and Alkylation of AMA-1B

Purified and refolded AMA-1 B was incubated for 60 min at 37° C. in the presence of 10 mM dithiothreitol and then for a further 60 min after the addition of iodoacetic acid to give a final concentration of 50 mM. The reduced and alkylated protein was then buffer-exchanged into phosphate-buffered saline by passage through a PD-10 column (Pharmacia) equilibrated with this buffer. The refolded AMA-1 B was aliquoted and then stored at −70° C.

Immunization of Mice

Refolded or reduced and alkylated AMA-1 B was emulsified with adjuvant (the Seppic adjuvant Montanide ISA 720 or Freund's complete and then incomplete adjuvant) and used to immunize C3H/He or BALB/c inbred mice (obtained from the Walter & Eliza Hall Institute breeding facility) or Swiss outbred mice (obtained from the Animal Resources Centre in Perth). Each mouse was immunized subcutaneously or intraperitoneally with a total of 20 ug protein on three occasions at four week intervals.

Challenge of Mice with *P. chabaudi adami* DS Strain

Two weeks after the third immunization C3H/He mice were challenged with $5 \times 10^6$ infected mouse erythrocytes. In a second trial BALB/c mice were challenged 1 week after the third immunization with $5 \times 10^5$ infected erythrocytes. In a third trial, outbred Swiss mice were challenged with $5 \times 10^5$ infected erythrocytes. In all trials infected erythrocytes for challenge were obtained from a mouse with a parasitaemia between 5–20%. Prior to challenge, mice in the immunized and control groups were ear clipped with a code number and randomly assigned to groups of 5–8 in different mouse boxes. Parasitaemias were monitored by microscopic examination of Giemsa stained smears prepared with a drop of blood obtained by piercing a tail vein. In trials 1 and 2, when mice exhibited symptoms of malaria they were examined twice daily and moribund mice were killed. Despite this policy some mice died in the period between observations. In trial 3, with permission from the Royal Melbourne Hospital Campus Animal Ethics Committee, mice were allowed to die without intervention.

Results

Expression and Purification of AMA-1

Figure 1:
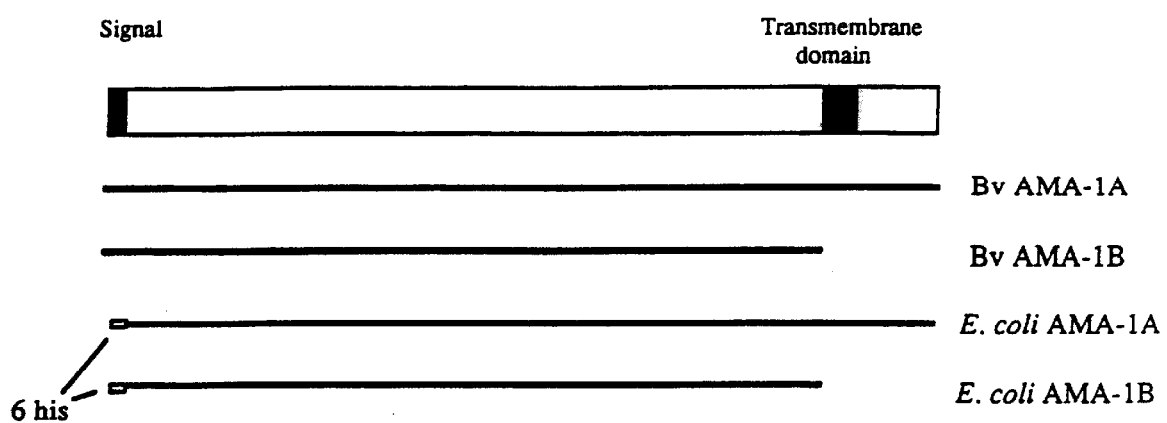

The full-length *P. chabaudi* AMA-1 (AMA-1A) and the ectodomain (AMA-1B) have been expressed in *E. coli* and in insect cells using recombinant baculovirus (FIG. 1). The oligonucleotide primers used for amplifying the *P. chabaudi* DNA were chosen so that both forms of AMA-1 expressed using baculovirus included the $NH_2$-terminal signal sequence, whereas both *E. coli* expressed forms of AMA-1 lacked the signal sequence.

Figure 2:
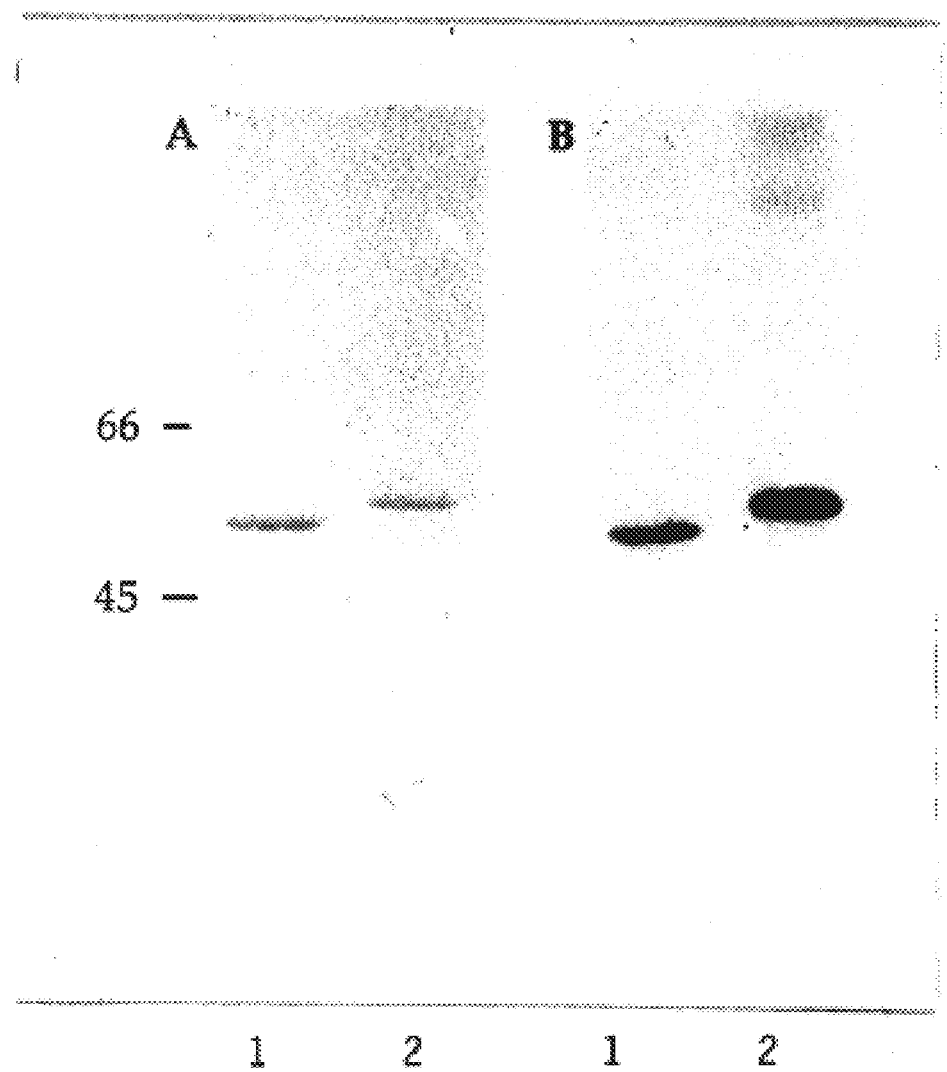

*P. chabaudi* AMA-1A and AMA-1B both formed insoluble inclusion bodies when expressed in *E. coli* with $NH_2$-terminal extensions that included a hexahistidine sequence. AMA-1B has been purified by isolating and washing the inclusion bodies, solubilisation in 6M guanidine-HCl and then Ni-chelate chromatography (FIG. 2). Although not free of minor contaminants, the protein eluted from the Ni-agarose column was considered suitable for preliminary refolding experiments and vaccination trials. At this stage no attempt has been made to purify *P. chabaudi* AMA-1A expressed in *E. coli*.

Refolding of AMA-1B

*P. chabaudi* AMA-1B was refolded in the presence of oxidized and reduced glutathione after being diluted 1:100- fold out of 6 M guanidine-HCl to give a final protein concentration of ~50 ug/ml. Several lines of evidence indicated that disulphide-dependent refolding had taken place. First, AMA-1B diluted into the refolding buffer remained in solution whereas if diluted into the same buffer lacking the oxidized and reduced glutathione much of the protein precipitated out of solution. Second, the refolded protein, when loaded in non-reducing sample buffer, migrated on SDS-PAGE as a relatively monodisperse band which contrasted with the polydisperse and aggregated nature of material which had not been subjected to the refolding procedure. Furthermore the major AMA-1 species seen in the refolded preparation migrated under non-reducing conditions with a slightly higher Mr than the same material analysed under reducing conditions (FIG. 2). Third, the refolded antigen was much more reactive with antibodies in the serum of hyperimmune mice when subjected to SDS-PAGE under nonreducing conditions rather than reducing conditions.

Immunogenicity and Antigenicity of Refolded AMA-1B

Figure 3:
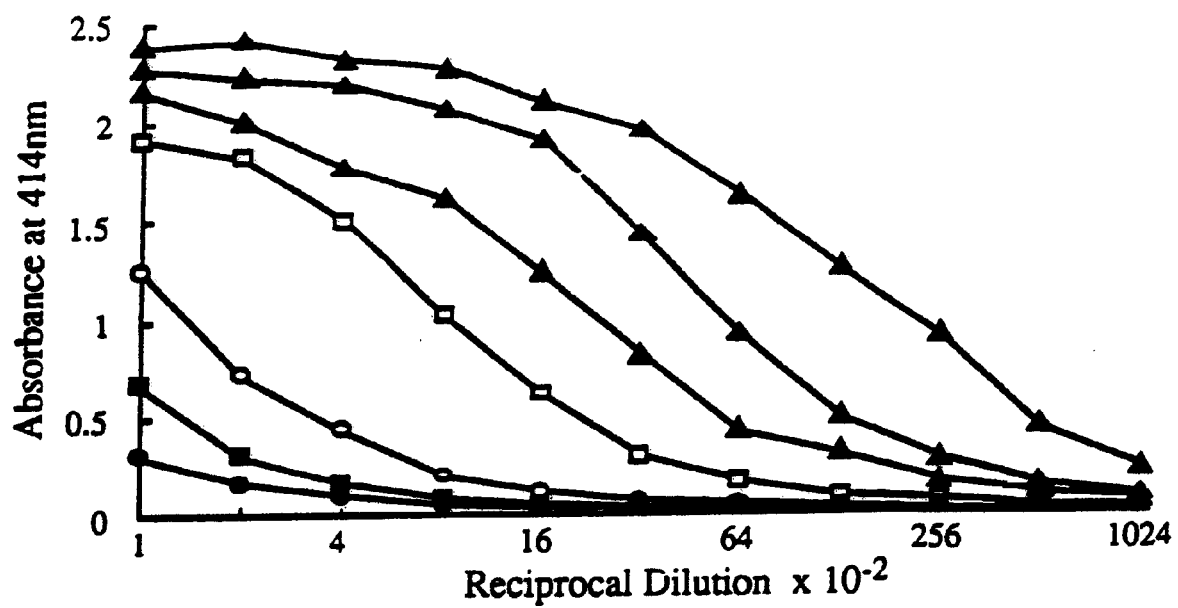
FIG. 3 shows anti-AMA-1B responses of a hyperimmune or an infected mouse against refolded (open squares and circles, respectively) or reduced and alkylated antigen (closed squares and circles, respectively) contrasted with the antibody responses against refolded AMA-1B induced by immunizing three mice with this antigen using Montanide ISA 720 as adjuvant (closed triangles).

The antigenicity of the refolded AMA-1B, demonstrated in immunoblots was examined further by ELISA. Serum from mice which had recovered from a single infection had relatively low titres of antibodies but recognized the refolded antigen in preference to the reduced and alkylated antigen. Mice which had been multiply infected had considerably higher antibody titres and again preferentially reacted with the refolded antigen. Rabbits and mice immunized with the refolded AMA-1B had higher antibody titres than did infected mice and also preferentially reacted with the refolded antigen (FIG. 3).

Immunization Trials

Trial 1

The geometric mean and range for the peak parasitaemias, the day of peak parasitaemia and mortality data for the five groups of mice in the first trial are shown in Table 1. Control mice had high parasitaemias with the peak parasitaemia occurring on day 8 or 9 in most animals (Group 1, Table 1). Most of these mice died or were killed when moribund. No protection was evident in mice immunized with a lysate of insect cells expressing AMA-1A or AMA-1B (Groups 2 & 3, Table 1) This was in contrast to the results of an earlier trial in which a different batch of cell lysate containing AMA-1A protected mice. The eight mice immunized with the refolded AMA-1B all survived with seven mice having dramatically reduced parasitaemias compared to control mice. Six of the eight mice had peak parasitaemias which ranged from 0.1–3.7% between day 7 and 15 after challenge (Group 4, Table 1). One mouse had no parasites detected at any time during the observation period after challenge. The eighth mouse had a peak parasitaemia of 72% on day 11 after challenge. In contrast to the very clear protective effect of immunization with the refolded AMA-1B, immunization with the reduced and alkylated AMA-1B did not provide any protection (Group 5, Table 1). The majority of the mice immunized with the reduced and alkylated antigen died or were killed moribund. These mice and the few surviving mice had high parasitaemias equivalent to those seen in the control mice.

Figure 4:
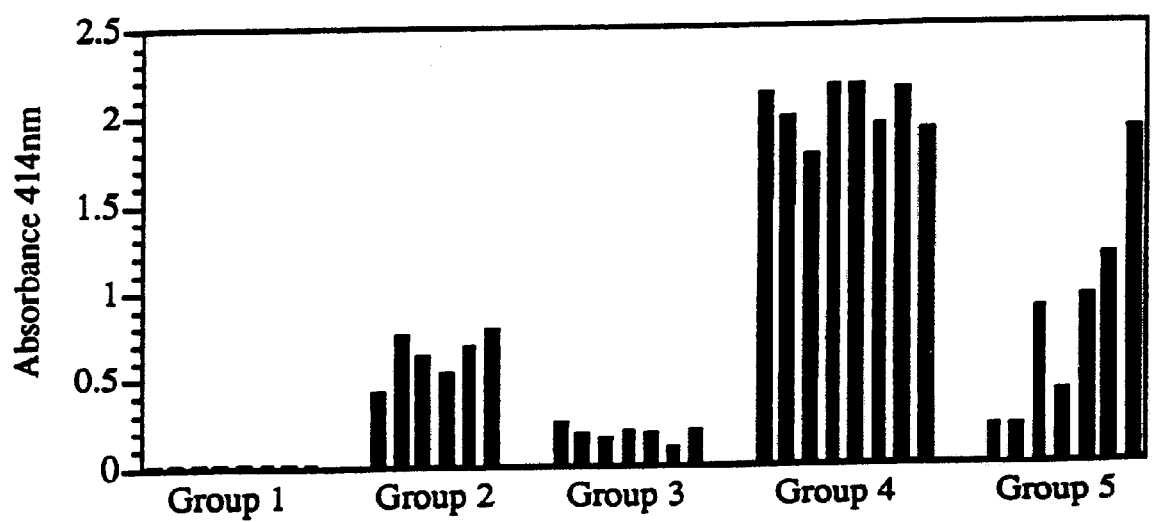
FIG. 4 shows antibody responses in Trial 1. The sera were diluted 1:10,000 and assayed using microtitre trays coated with the refolded AMA-1B.

The antibody responses induced by the various forms of AMA-1 were determined by ELISA using the refolded AMA-1B to coat microtitre plates. The highest antibody levels after the third immunization, prior to challenge with *P. chabaudi*, were in the mice immunized with the *E. coli*-expressed AMA-1B that had been refolded—the only group of mice which was protected (FIG. 4). Significant antibody levels were detected in mice immunized with both forms of AMA-1 expressed in insect cells, however, the levels were lower than those in mice protected in a previous trial by immunization with an insect cell lysate containing AMA-1A. Although, the antibody levels in some mice immunized with the reduced and alkylated antigen approached those in the mice immunized with the refolded antigen it is assumed that the fine specificity of these antibodies would be very different from those induced by the refolded AMA-1B.

TABLE 1

Trial 1 Summary

| Group | Peak Parasitaemia | | | Outcome |
|---|---|---|---|---|
| | Mean* | Range | Day | |
| 1. Control- Insect cell lysate plus ISA 720 | 47.4 | 20.3–82.4 | 8–13 | 2 of 8 survived |
| 2. AMA-1A Insect cell lysate plus ISA 720 | 45.4 | 18.6–69 | 9–11 | None survived |
| 3. AMA-1B Insect cell lysate plus ISA 720 | 44.8 | 10.8–70.2 | 8–9 | 2 of 7 survived |
| 4. Refolded *E. coli* AMA-1B plus ISA 720 | 1.09 | 0–72.5 | 7–16 | All 8 survived |
| 5. Red. & Alk. *E. coli* AMA-1B plus ISA 720 | 40.6 | 15.5–>90 | 9–13 | 3 of 7 survived. |

*Geometric means - One mouse in group 5 in which no parasites were detected at any stage was assumed to have a peak parasitaemia of 0.05% for the calculation of the geometric mean peak parasitaemia.

Trial 2

In this trial the immunizing efficacy of refolded AMA-1B was assessed with two different adjuvants; Montanide ISA 720 and Freund's adjuvant. Control mice received either adjuvant alone or no treatment. In contrast to the first trial which was carried out using C3H/He (H2$^k$) mice, BALB/c (H2$^d$) mice were used for the second trial. An additional difference between the two trials was the number of infected erythrocytes used for challenge, being 5×10$^6$ and 5×10$^5$ for the first and second trials, respectively. As in the first trial, immunization with AMA-1B provided very clear protection against challenge with *P. chabaudi adami*. Of the 11 control mice nine either died or were killed moribund whereas only one of the 11 immunized mice did not survive. Protection was achieved formulating the antigen with either adjuvant. The one immunized mouse that died received the antigen formulated with Freund's adjuvant but group sizes were too small to determine whether one adjuvant was better than the other. As in the first trial, there was one immunized mouse in which no parasites were detected throughout the trial.

TABLE 2

Trial 2 Summary

| Group | Peak Parasitaemia | | | Outcome |
|---|---|---|---|---|
| | Mean* | Range | Day | |
| 1. Control- No treatment | 41.0 | 27.6–52 | 8–9 | 1 of 3 survived |
| 2. Control - FCN/IFA | 52.0 | 46.7–58 | 7–8 | 1 of 4 survived |
| 3. Control - ISA 720 | 44.5 | 36.9–50.1 | 7–9 | 0 of 4 survived |
| 4. Refolded AMA-1B plus FCN/IFA | 2.16 | 0.1–52.9 | 3–11 | 4 of 5 survived |

TABLE 2-continued

Trial 2 Summary

| | | Peak Parasitaemia | | |
|---|---|---|---|---|
| Group | Mean* | Range | Day | Outcome |
| 5. Refolded AMA-1B plus ISA 720 | 0.87 | 0–34 | 3–9 | All 6 survived. |

*Geometric means - One mouse in group 5 in which no parasites were detected at any stage was assumed to have a peak parasitaemia of 0.05% for the calculation of the geometric mean peak parasitaemia.

Trial 3

In this trial the immunizing efficacy of refolded AMA-1B was assessed in outbred mice using the adjuvant Montanide ISA-720 and larger groups of mice than in the previous trials. Eighteen mice were immunized with the refolded AMA-1B (Group 3, Table 3) and the course of the infections in these mice were compared with the infections in 20 control mice which were divided into two groups of 10, one of which (Group 2, Table 3) was immunized with reduced and alkylated AMA-1B in the Montanide ISA-720 adjuvant and the other of which (Group 1, Table 3) received the adjuvant alone.

As with the immunized inbred mice used in previous trials, there was very clear evidence that immunization of the outbred mice with the refolded AMA-1B provided substantial protection against challenge with P. chabaudi adami with the geometric mean peak parasitaemia of these mice being 2.86% compared with a geometric mean peak parasitaemia of 55.5% for the mice receiving adjuvant alone. Again, as seen with inbred mice, immunization with the reduced and alkylated AMA-1B failed to provide significant protection. Although there was no overlap of peak parasitaemias between the immunized and control mice, nevertheless, within the group of mice immunized with the refolded AMA-1B peak parasitaemias covered a wide range with no parasites being detected in 3 mice but with 3 other mice having a peak parasitaemias above 20% (Table 3).

TABLE 3

Trial 3 Summary

| | | Peak Parasitaemia | | |
|---|---|---|---|---|
| Group | Mean | Range | Day | Outcome |
| 1. ISA 720 alone | 55.5 | 43.9–66.7 | 7–10 | 4 of 10 survived |
| 2. Reduced & alkylated AMA-1B plus ISA 720 | 53.7 | 37.9–67.7 | 7–8 | 8 of 10 survived |
| 3. Refolded AMA-1B plus ISA 720 | 3.96 | 0–34.1 | 8–18 | 17 of 18 survived |

*Geometric means - Three mice in group 3 in which no parasites were detected at any stage was assumed to have a peak parasitaemia of 0.05% for the calculation of the geometric mean peak parasitaemia.

Summary of Trials

The trials in mice have given consistent results showing that it is possible to protect mice by immunization with the $NH_2$-terminal domain of P. chabaudi AMA-1 expressed in E. coli. The great majority of immunized mice had peak parasitaemias which were dramatically lower than those seen in control mice. In each of trials 1 and 2, there was one mouse in which no parasites were seen throughout the period of observation. Of a total of 37 mice in the three trials immunized with the refolded E. coli-expressed AMA-1B, only two mice died whereas 21 of 29 control mice in the three trials died and 17 of the 30 mice immunized with other forms of AMA-1 died.

EXAMPLE 2

P. falciparum AMA-1

Materials and Methods

Expression of P. falciparum AMA-1B

DNA encoding the ectodomain of the AMA-1 from the human parasite P. falciparum, clone 3D7 of the NF54 isolate, was amplified from genomic DNA using a mixture of Pfu DNA polymerase (Stratagene) and AmpliTaq DNA polymerase (Perkin Elmer Cetus) in the ratio 1:1. The oligonucleotides used for amplification corresponded to nucleotides 406–430 (SEQ ID NO: 3) and 1945–1968, (SEQ ID NO: 4) of the published sequence[4]. The 5' oligonucleotide (nucleotides 406–430(SEQ ID NO: 3) contained a restriction site for BamH1, and the 3' oligonucleotide (nucleotides 1945–1968(SEQ. ID NO: 4) contained a restriction site for Pst1. The amplified DNA was digested with BamH1 and Pst1, gel purified, ligated into the expression vector PDS56/RBSII, 6×His and transformed into cells of the E. coli strain JPA101.

Purification and Refolding of Recombinant P. falciparum AMA-1B

Essentially identical methods were used to isolate and refold recombinant P. falciparum AMA-1B as are described for the P. chabaudi adami antigen in Example 1. However, because the P. falciparum antigen has a lower isoelectric point it is possible to refold the purified protein at a lower ionic strength (e.g. 10 mM Tris-HCl, 20 mM NaCl, pH 8.0). This means that dialysis is not required before the sample can be bound to DEAE-Sepharose or other anion-exchangers for further purification. Reversed-phase high pressure liquid chromatography (RP-HPLC) experiments were carried out using a Hewlett Packard HP 1050 modular HPLC instrument consisting of on-line solvent degasser, quaternary pumps, rheodyne manual injector and diode array detector. Detector signals were analysed by HP Chem Stations V2.0 software. Brownlee C18 and C8 2.1×30 mm cartridge type columns were used throughout.

Results

Expression and Preliminary Purification of P. falciparum AMA-1B

Figure 5:
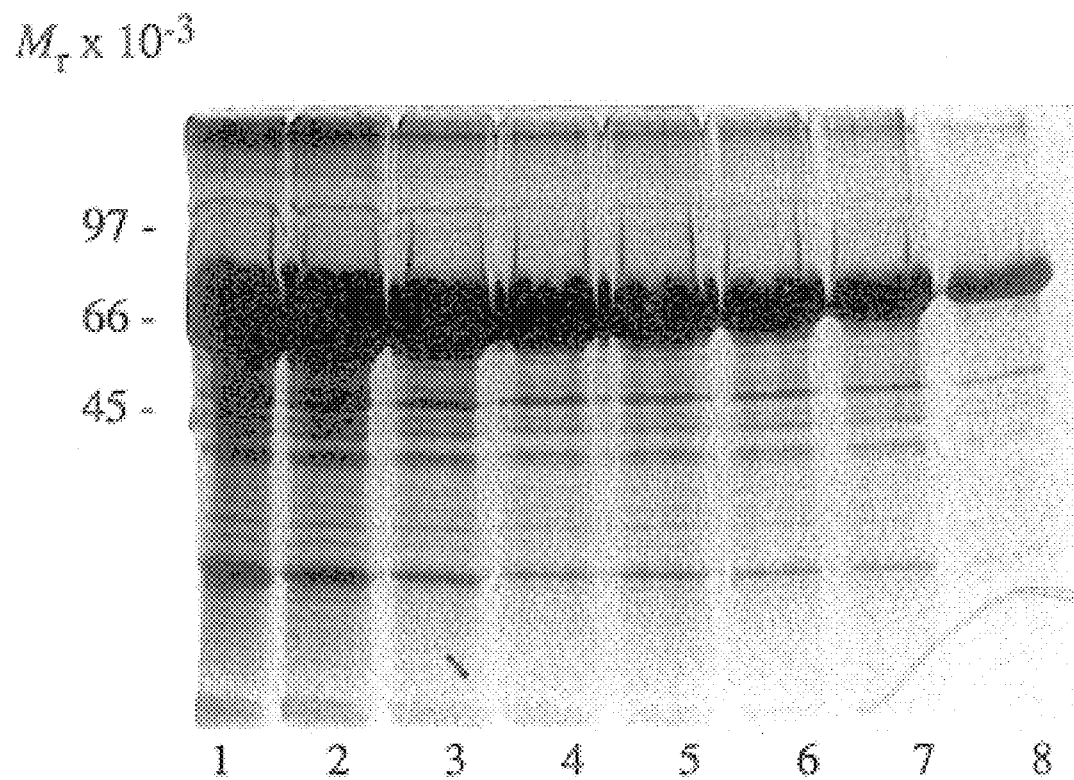
FIG. 5 shows SDS-PAGE of eight consecutive fractions containing *P. falciparum* AMA-1 B obtained by eluting a 10 ml column of Ni-agarose with 6M guanidine-HCl, 10 mM tris-HCl, pH 4.5.

The ectodomain (AMA-1B) of P. falciparum AMA-1 was expressed in E. coli as an abundant inclusion body. Washed inclusion bodies were solubilised in 6M guanidine-HCl and the AMA-1B isolated in semi-purified form by Ni-chelate chromatography. As for the P. chabaudi AMA-1B, the P. falciparum AMA-1B eluted in high yield from the column of Ni-agarose in buffer adjusted to pH 4.5 (FIG. 5).

Refolding and Further Purification of P. falciparum AMA-1B

The P. falciparum AMA-1B eluted from the Ni-agarose column was refolded using conditions equivalent to those used for refolding the P. chabaudi antigen except that prior to initiating refolding the P. falciparum antigen was usually reduced by incubation at 37° C. for 30 minutes in the presence of 10 mM dithiothreitol. The effect of refolding on the antigenicity of the P. falciparum AMA-1B was examined by immunoblot analyses of reduced and non-reduced SDS-polyacrylamide gels. When the blots were probed with a pool of human sera obtained from adults living in an area endemic for malaria it was clear that the refolded antigen electrophoresed under non-reducing conditions (FIG. 6, lane 3) reacted more strongly with the human antibodies than did the nonfolded or the reduced and alkylated antigen electrophoresed under non-reducing conditions (FIG. 6, lanes 1 and 2) or any of the antigens electrophoresed under reducing conditions (FIG. 6, lanes 4–6).

Because it will be necessary to have highly purified *P. falciparum* AMA-1B for testing vaccine efficacy in clinical trials the feasibility of using RP-HPLC for purification of refolded AMA-1B has been explored. AMA-1B can be recovered from a C18 RP column using an acetonitrile gradient. Material which had not been refolded eluted in three major peaks with retention times between 22 and 27 minutes with the majority of the sample in the last eluting of these peaks. An additional series of minor peaks with longer retention times were also evident with the unfolded sample. Material subjected to the refolding protocol had a very different elution profile with the majority of the sample eluting with a retention time equivalent to the earliest eluting peak in the unfolded sample. Thus RP-HPLC will provide an additional purification step if one is required to reach the purity specification applicable to antigen to be used in clinical trials. In addition, it appears that RP-HPLC will be useful for removal of unfolded AMA-1B or folding intermediates from the refolded protein.

EXAMPLE 3

*P. vivax* AMA-1

Materials and Methods

Expression of *P. vivax* AMA-1B

DNA encoding the ectodomain of the AMA-1 for the human parasite *P. vivax*, isolate PH84 from the Philippines, was amplified from genomic DNA using AmpliTaq DNA polymerase (Perkin Elmer Cetus). The oligonucleotides used contained restriction sites for Bgl II at the 5' end and Sac I at the 3' end. The amplified DNA corresponded to bases 49-1452 (SEQ ID NO:5) of the published sequences[10]. The amplified DNA was cloned into the plasmid pUC18 and clones were sequenced. As all clones sequenced contained at least one point mutation, further subcloning was undertaken to combine portions of a number of clones to generate a mutation free clone of the AMA-1B gene. This insert was amplified with a 1:1 mixture of Pfu DNA polymerase (Stratagene) and AmpliTaq DNA polymerase (Perkin Elmer Cetus), digested with Bgl II and Sac I, gel purified and ligated into the expression vector pTrcHis A (Invitrogen) and transformed into cells of the *E. coli* strain Sure.

Purification and Refolding of Recombinant *P. vivax* AMA-1B

Essentially identical methods were used to isolate and refold recombinant *P. vivax* AMA-1B as are described for the *P. falciparum* antigen in Example 2.

Results

Expression and Preliminary Purification of *P. vivax* AMA-1B

The ectodomain (AMA-1B) of *P. vivax* AMA-1 was expressed in *E. coli* as an abundant inclusion body. Washed inclusion bodies were solubilised in 6M guanidine-HCl and the AMA-1B isolated is semi-purified form by Ni-chelate chromatography. As for the *P. falciparum* AMA-1B, the *P. vivax* AMA-1B eluted in high yield from the column of Ni-agarose in buffer adjusted to pH 4.5 (FIGS. 7 and 8).

Refolding and Further Purification of *P. vivax* AMA-1B

The *P. vivax* AMA-1B eluted from the Ni-agarose column is refolded and further purified using conditions equivalent to those described for refolding the *P. falciparum* antigen in Example 2.

REFERENCES:

1. Deans, J. A., Alderson, T., Thomas, A. W., Mitchell, G. H., Lennox, E. S. and Cohen, S. (1982). Rat monoclonal antibodies which inhibit the in vitro multiplication of *Plasmodium knowlesi*. *Clin Exp Immunol* 49, 297–309.
2. Thomas, A. W., Deans, J. A., Mitchell, G. H., Alderson, T. and Cohen, S. (1984). The Fab fragments of monoclonal IgG to a merozoite surface antigen inhibit *Plasmodium knowlesi* invasion of erythrocytes. *Mol Biochem Parasitol* 13, 187199.
3. Deans, J. A., Knight, A. M., Jean, W. C., Waters, A. P., Cohen, S. and Mitchell, G. H. (1988). Vaccination trials in rhesus monkeys with a minor, invariant, *Plasmodium knowlesi* 66 kD merozoite antigen. *Parasite Immunol* 10, 535–552.
4. Peterson, M. G., Marshall, V. M., Smythe, J. A., Crewther, P. E., Lew, A., Silva, A., Anders, R. F. and Kemp, D. (1989). Integral membrane protein located in the apical complex of *Plasmodium falciparum*. *Mol Cell Biol.* 9, 3151–3154.
5. Thomas, A. W., Waters, A. P. and Carr, D. (1990). Analysis of variation in Pf83, an erythrocytic merozoite vaccine candidate antigen of *Plasmodium falciparum*. *Mol Biochem Parasitol* 42, 285–288.
6. Marshall, V. M., Peterson, M. G., Lew, A. M. and Kemp, D. J. (1989). Structure of the apical membrane antigen I (AMA-1) of *Plasmodium chabaudi*. *Mol Biochem Parasitol* 37, 281–3.
7. Peterson, M. G., Nguyen-Dinh, P., Marshall, V. M., Elliott, J. F., Collins, W. E., Anders, R. F. and Kemp, D. J. (1990). Apical membrane antigen of *Plasmodium fragile*. *Mol Biochem Parasitol* 39, 279–83.
8. Waters, A. P., Thomas, A. W., Deans, J. A., Mitchell, G. H., Hudson, D. E., Miller, L. H., McCutchan, T. F. and Cohen, S. (1990). A merozoite receptor protein from *Plasmodium knowlesi* is highly conserved and distributed throughout *Plasmodium*. *J Biol Chem* 265, 17974–17979.
9. Sambrook, J., Fritsch, E. F. and Maniatis, T. (1989) *Molecular Cloning: A Laboratory Manual.* 2nd edition. Cold Spring Harbor Laboratory Press, Cold Spring Harbor, p. 17–37.
10. Cheng, Q. and Saul, A. (1994). Sequence analysis of the apical membrane antigen I (AMA-I) of *Plasmodium vivax*. *Mol. Biochem. Parasitol.* 65: 183–187.

What is claimed is:

1. A DNA expression vector comprising a polynucleotide encoding a polypeptide consisting of AMA-1B or fragments thereof from plasmodium species *P. falciparum* or *P. vivax*, and wherein said AMA-1B polypeptide contains 16 conserved cysteine residues and said fragments thereof are comprised of from 2 to 16 conserved cysteine residues of a mature ectodomain of apical membrane antigen (AMA-1).

2. A host cell containing the DNA expression vector according to claim 1.

3. A host cell according to claim 2, which is selected from the group consisting of *E. coli* insect cells, and yeast.

4. An isolated AMA-1B polypeptide or fragments thereof from plasmodium species *P. falciparum* or *P. vivax*, wherein said AMA-1B polypeptide contains 16 conserved cysteine residues and said fragments thereof are comprised of from 2 to 16 conserved cysteine residues of a mature ectodomain of apical membrane antigen-1 (AMA-1) and said AMA-1B polypeptide or fragments thereof are stabilized by generating intramolecular disulphide bonds.

5. The AMA-1B polypeptide of claim 4.

6. A composition comprising the AMA-1B polypeptide or fragments thereof of claim 4, and a carrier.

7. A composition comprising the AMA-1B polypeptide of claim 5, and a carrier.

8. A method of producing antibodies in a host against Plasmodium species *P. falciparum* or *P. vivax*, which method comprises administering to the host the AMA-1B polypeptide or fragments thereof of claim 4.

9. A method for immunizing a host against Plasmodium parasitemia which comprises administering to a host an effective amount of the composition of claim 7.

10. A method for eliciting an immune response in a host against Plasmodium parasitemia which comprises administering to a host an effective amount of the composition of claim 7.

* * * * *